United States Patent [19]

Breant

[11] 4,419,282

[45] Dec. 6, 1983

[54] N,N-DIMETHYLOCTANAMIDE FRAGRANCES

[75] Inventor: Claude Breant, Villeurbanne, France

[73] Assignee: Rhone-Poulenc Industries, Paris, France

[21] Appl. No.: 302,673

[22] Filed: Sep. 15, 1981

[30] Foreign Application Priority Data

Sep. 26, 1980 [FR] France ............................... 80 20984

[51] Int. Cl.[3] ........................... A61K 7/46; C11B 9/00

[52] U.S. Cl. ........................... 252/522 R; 252/174.11; 424/65; 424/73

[58] Field of Search .......... 252/522 R, 522 A, 174.11; 424/65, 73

[56] References Cited

U.S. PATENT DOCUMENTS 3,576,728 4/1971 Smith .............................. 204/181 P 4,228,044 10/1980 Cambre .............................. 252/547

OTHER PUBLICATIONS

Davydova et al., Chem. Absts., vol. 73, No. 65414g, (1970).

A. S. Lutta et al., *Entomol. Obozremie.* 45, 317–25, (1966).

*Primary Examiner*—John F. Niebling

*Attorney, Agent, or Firm*—Burns, Doane, Swecker & Mathis

[57] ABSTRACT

Scents and perfumed compositions include, as an odorant therefor, an olfactory affecting amount of N,N-dimethyloctanamide.

16 Claims, No Drawings

N,N-DIMETHYLOCTANAMIDE FRAGRANCES

CROSS-REFERENCE TO RELATED APPLICATIONS

My copending application, Ser. No. 136,545, filed Apr. 2, 1980, now U.S. Pat. No. 4,301,201, and application Ser. No. 302,672, filed concurrently herewith, both assigned to the assignee hereof.

BACKGROUND OF THE INVENTION

1. Field of the Invention:

The present invention relates to novel scents and perfume compositions including novel perfume bases, and, more especially, to such scents and perfume compositions comprised of the odorant, N,N-dimethyloctanamide.

2. Description of the Prior Art:

The use of certain alkanoic acid amides for incorporation into perfume or insect repellent compositions has already been proposed to this art, but not one of such amides is either distinguished or characterized by any unique or original fragrance evoking a pleasant olfactory response. Thus, Einhorn et al, Ber., 39, 1,223 (1906) report that N,N-diethyl-2-ethylbutanamide evolves n a faint scent akin to that of menthol; French Pat. No. 1,572,332 notes that N,N-diethyldimethylpropanamide has a peppermint fragrance, while N,N-dimethyl-2-ethylbutanamide emits the fragrance of natural mint. In U.S. Pat. No. 3,909,462 there is attributed to N-phenyl-N-methyl-2-ethylbutanamide the odor of grapefruit utilized in the formulation of food and herb aromas to develop a composition suitable for use as a base in perfumes having a lavender fragrance. Finally, A. S. Lutta et al, Entomol. Obozrenie, 45, 317-25 (1966) noted in a study of the insect repellent properties of the alkanamides, the agreeable odor of N,N-diethyloctamide, without reflecting upon any specific fragrance. It has since been determined that this particular amide has a weakly spicy odor that is relatively common. It too has been definitely ascertained that the amides of the $C_5$-$C_6$ alkanoic acids, with the exception of N-phenyl-N-methyl-2-ethylbutanamide, emit the more or less common mint odors. Furthermore, for a given acid, the character of the fragrance varies in direct response to the nature of the substituents borne by the amido nitrogen atom, but without, however, the ultimate fragrance evolved being at all predictable; thus, N,N-dimethyl-2-ethylbutanamide emits the fresh scent of natural mint, far stronger than that of the N,N-diethyl homolog, the scent of which latter derivative even though also being that of mint, being much weaker and more akin to that of peppermint. On the other hand, the molecular structure of the acid significantly affects the fragrance of the amide; thus, N,N-diethylcaprylamide evolves a scent considerably different from that of N,N-diethyl-2-ethylbutanamide. It logically follows, therefore, that it is difficult, if not impossible for those skilled in this art to reliably predict whether or not a given alkanamide will have a pleasing odor from an olfactory sensation point of view and, if so, just what that particular fragrance would be.

Accordingly, the perfume industry is continously seeking novel odorants and fragrances which by virtue of their uniqueness, availability, volatility and strength of scent are well adapted for formulation into perfume compositions which are completely unique.

SUMMARY OF THE INVENTION

Accordingly, a major object of the present invention is the provision of a novel odorant, and scents and perfume compositions/formulations comprised thereof, all of which are characterized by an originally unique fragrance.

Briefly, the present invention features novel scents and perfume compositions/formulations, whether perfume bases or final perfume products, each of which is characterized in that, in addition to the typical perfume ingredients or components comprising same, if any, such products contain an effective fragrant, or fragrance attentuating amount of the odorant, N,N-dimethyloctanamide.

DETAILED DESCRIPTION OF THE INVENTION

More particularly, the present invention features scents and perfume compositions/formulations, and perfume bases and perfumed products, each of which is characterized by including, as the active ingredient odorant thereof, an effective olfactory affecting amount of N,N-dimethyloctanamide.

N,N-dimethyloctanamide, which has the structural formula:

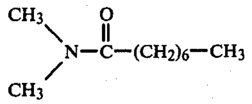

emits or gives off a slightly spicy, oily, sharp odor, associated with the scent of jasmine and of lavender, which makes it especially valuable for floral, fougère or lavender bases, thus imparting more natural freshness and a spicy characteristic thereto.

By the expressions "perfume composition", "scent" or "formulation" any admixture of the different perfume ingredients, such as the typical solvents, solid or liquid perfume carriers, fixing agents, any one or more of the known fragrances or scents, and the like, and with which the N,N-dimethyloctanamide is formulated or incorporated, such admixtures being utilized to impart to any type of substrate, or finished or final product, the particular fragrance desired. The perfume bases constitute preferred examples of the perfume compositions consistent herewith wherein the N,N-dimethyloctanamide may be used to advantage. Other compositions wherein the subject compound may advantageously be incorporated are the conventional detergent compositions. These compositions typically comprise one of more of the following ingredients: anionic, cationic or amphoteric surface active agents, bleaching agents, optical bluing or whitening agents, fluorescent brighteners, various fillers and anti-redeposition ingredients. The nature of these different ingredients is not critical and the N,N-dimethyloctanamide may be added to any type of detergent. Toilet waters, after-shave lotions, perfumes, soaps and deodorant and sanitary products, for example in aerosol form, are exemplary of those substrates and final products which can be uniquely scented with N,N-dimethyloctanamide according to this invention.

N,N-dimethyloctanamide is itself a colorless liquid, boiling at 96° C. under a pressure of 2 mm Hg, and is very soluble in the conventional organic solvents, such as the alcohols, ketones, esters or ethers.

The amount of N,N-dimethyloctanamide in the various compositions according to the invention, expressed in percentage by weight in the particular composition under consideration, strictly depends on the nature of each such composition (perfume or toilet water base, for example) and the nature and intensity of the fragrance desired in the final product. It is thus obvious that in a perfume base the amount of N,N-dimethyloctanamide may be very high, for example, higher than 50% by weight, and as much as 90% by weight, while in a perfume, a toilet water, an after-shave lotion or a soap, such amount may be considerably lower than 50% by weight. Thus, for all practical purposes the lower limit on the amount of N,N-dimethyloctanamide is that amount which effects a perceptible modification in the odor, fragrance, or scent of the final product. In certain cases, this minimum amount may be on the order of 0.01% by weight. Obviously, amounts without the aforenoted range too may be utilized without departing from the scope of the present invention.

Moreover, the N,N-dimethyloctanamide incorporated per the invention is itself conveniently prepared by simply reacting an octanoyl halide with dimethylamine in the presence of an aqueous solution of an alkali metal base (preferably sodium or potassium).

In order to further illustrate the present invention and the advantages thereof, the following specific Examples are given, it being understood that same are intended only as illustrative and in nowise limitative.

EXAMPLE 1

300 g of N,N-dimethyloctanamide were added to the following floral base:

| | | |
|---|---|---|
| (i) | Bergamot oil | 40 |
| (ii) | Eugenol | 30 |
| (iii) | Anisylpropanal | 40 |
| (iv) | Piperonylpropanal | 50 |
| (v) | Anisaldehyde diethylacetal | 100 |
| (vi) | Phenylethyl alcohol | 120 |
| (vii) | Alpha-hexylcinnamaldehyde | 100 |
| (viii) | Benzyl acetate | 120 |
| (ix) | Nonyl acetate | 100 |
| | | 700 g |

and the composition obtained was compared with the base formulation.

N,N-dimethyloctanamide strengthens the floral bouquet, imparting a fresh and spicy character to the composition.

EXAMPLE 2

300 g of N,N-dimethyloctanamide were added to the following fougere base:

| | | |
|---|---|---|
| (i) | Lavandin oil | 110 |
| (ii) | Aspic oil | 35 |
| (iii) | Geraniol | 100 |
| (iv) | Oakmoss absolute | 15 |
| (v) | Coumarin | 25 |
| (vi) | Patchouli oil | 15 |
| (vii) | Amyl salicylate | 100 |
| (viii) | Xylene musk | 20 |
| (ix) | Linalyl acetate | 100 |
| (x) | Total rhodinone | 60 |
| (xi) | Heliotropine | 20 |
| (xii) | Bergamot oil | 50 |
| (xiii) | Lemon oil | 50 |

-continued

| | | |
|---|---|---|
| | | 700 g |

and the composition obtained was compared with the base formulation.

N,N-dimethyloctanamide strengthens the scent of lavender, imparts a flowery and fresh characteristic and diminishes the harsh bouquet of the base formulation.

EXAMPLE 3

300 g of N,N-dimethyloctanamide were added to the following lavender base:

| | | |
|---|---|---|
| (i) | Lavender oil | 250 |
| (ii) | Lavindin oil | 150 |
| (iii) | Aspic oil | 50 |
| (iv) | Coumarin | 25 |
| (v) | Ketone L | 5 |
| (vi) | Linalyl acetate | 100 |
| (vii) | Terpenyl acetate | 120 |
| | | 700 g |

and the composition obtained was compared with the base formulation.

N,N-dimethyloctanamide imparts the natural scent of lavender to the composition, diminishing the composite effect of the base formulation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a perfumed composition, the improvement which comprises, as an odorant therefor, an effective fragrance imparting amount of N,N-dimethyloctanamide.

2. The perfumed composition as defined by claim 1, the same comprising at least one other fragrance in addition to said N,N-dimethyloctanamide.

3. The perfumed composition as defined by claims 1 or 2, the same comprising a perfume solvent.

4. The perfumed composition as defined by claims 1 or 2, the same comprising a solid or liquid perfume carrier.

5. The perfumed composition as defined by claims 1 or 2, the same comprising a fixing agent.

6. The perfumed composition as defined by claim 1, comprising a detergent or soap.

7. The perfumed composition as defined by claim 1, comprising a toilet water.

8. The perfumed composition as defined by claim 1, comprising an after-shave lotion.

9. The perfumed composition as defined by claim 1, comprising a deodorant.

10. The perfumed composition as defined by claim 1, comprising a liquid perfume.

11. The perfumed composition as defined by claim 6, further comprising at least one member selected from the group consisting of a surfactant, a bleaching agent, an optical bluing or whitening agent, a fluorescent brightener, a filler and an anti-redeposition agent.

12. The perfumed composition as defined by claim 1, comprising from 50% to 90% by weight of N,N-dimethyloctanamide.

13. The perfumed composition as defined by claim 1, comprising from 0.01% to 50% by weight of the N,N-dimethyloctanamide.

14. The method of perfuming a substrate comprising applying thereto an effective fragrance imparting amount of N,N-dimethyloctanamide.

15. The method of perfuming a substrate, comprising applying thereto the perfumed composition as defined by claim 1.

16. The method as defined by claims 14 or 15, said substrate being human skin.

* * * * *